(12) United States Patent
Hallaraker et al.

(10) Patent No.: US 10,076,530 B2
(45) Date of Patent: Sep. 18, 2018

(54) LIPID COMPOSITIONS WITH HIGH DHA CONTENT

(71) Applicant: Arctic Nutrition AS, Hovdebygda (NO)

(72) Inventors: Hogne Hallaraker, Volda (NO); Jan Remmereit, Volda (NO); Alvin Berger, Long Lake, MN (US)

(73) Assignee: Arctic Nutrition AS, Hovdebygda (NO)

( * ) Notice: Subject to any disclaimer, the term of this patent is extended or adjusted under 35 U.S.C. 154(b) by 0 days.

(21) Appl. No.: 15/283,971

(22) Filed: Oct. 3, 2016

(65) Prior Publication Data

US 2017/0079993 A1 Mar. 23, 2017

Related U.S. Application Data

(63) Continuation of application No. 14/498,548, filed on Sep. 26, 2014, now Pat. No. 9,458,409, which is a continuation of application No. 13/601,626, filed on Aug. 31, 2012, now Pat. No. 8,846,604.

(60) Provisional application No. 61/650,206, filed on May 22, 2012, provisional application No. 61/530,648, filed on Sep. 2, 2011.

(51) Int. Cl.
| | |
|---|---|
| *A61K 31/685* | (2006.01) |
| *A61K 31/661* | (2006.01) |
| *A61K 31/683* | (2006.01) |
| *A61K 9/00* | (2006.01) |
| *A61K 47/22* | (2006.01) |
| *A61K 9/06* | (2006.01) |
| *A61K 9/12* | (2006.01) |
| *A61K 47/44* | (2017.01) |
| *A61K 9/20* | (2006.01) |
| *C11B 1/10* | (2006.01) |
| *A23K 20/158* | (2016.01) |
| *A23K 50/80* | (2016.01) |
| *A23K 50/60* | (2016.01) |
| *A23L 33/115* | (2016.01) |
| *A61K 31/202* | (2006.01) |

(52) U.S. Cl.
CPC .......... *A61K 31/661* (2013.01); *A23K 20/158* (2016.05); *A23K 50/60* (2016.05); *A23K 50/80* (2016.05); *A23L 33/115* (2016.08); *A61K 9/0019* (2013.01); *A61K 9/06* (2013.01); *A61K 9/12* (2013.01); *A61K 9/2018* (2013.01); *A61K 9/2054* (2013.01); *A61K 31/202* (2013.01); *A61K 31/683* (2013.01); *A61K 31/685* (2013.01); *A61K 47/22* (2013.01); *A61K 47/44* (2013.01); *C11B 1/10* (2013.01)

(58) Field of Classification Search
None
See application file for complete search history.

(56) References Cited

U.S. PATENT DOCUMENTS

| | | | |
|---|---|---|---|
| 7,189,418 B2 | 3/2007 | Hiratsuka et al. | |
| 7,759,325 B2 | 7/2010 | Dupont | |
| 8,846,604 B2 * | 9/2014 | Hallaraker | A61K 31/683 |
| | | | 426/601 |
| 9,458,409 B2 * | 10/2016 | Hallaraker | A61K 31/683 |
| 2005/0130937 A1 | 6/2005 | Ben Dror et al. | |
| 2006/0128665 A1 | 6/2006 | Leigh et al. | |
| 2008/0089999 A1 | 4/2008 | Alpern | |
| 2008/0153782 A1 * | 6/2008 | Dupont | A61K 31/685 |
| | | | 514/76 |
| 2010/0143571 A1 | 6/2010 | Breivik | |
| 2010/0316680 A1 | 12/2010 | Bruheirn et al. | |
| 2011/0160161 A1 | 6/2011 | Sampalis et al. | |

FOREIGN PATENT DOCUMENTS

| | | | |
|---|---|---|---|
| JP | 2006311853 A | 11/2006 | |
| JP | 2008044907 A | 2/2008 | |
| JP | 2008255182 A | 10/2008 | |
| WO | 91013957 A1 | 9/1991 | |
| WO | 9221335 A1 | 12/1992 | |
| WO | 9739759 A2 | 10/1997 | |
| WO | 0023546 A1 | 4/2000 | |
| WO | 0078903 A1 | 12/2000 | |
| WO | 0150884 A1 | 7/2001 | |
| WO | 02102394 A2 | 12/2002 | |
| WO | 03011873 A2 | 12/2003 | |
| WO | 2004047554 A1 | 6/2004 | |
| WO | 2005037848 A2 | 4/2005 | |
| WO | 2005038037 A2 | 4/2005 | |
| WO | 2006054183 A2 | 5/2006 | |

(Continued)

OTHER PUBLICATIONS

Bechtel, P.J., et al, "Characterization of Protein Fractions from Immature Alaska Walleye Pollock (*Theragra chalcogramma*) Roe;" J Food Sci; 72(5):6338-5343; Jun. 2007.
Bekhit, A., et al., "Impact of Maturity on the Physicochemical and Biochemical Properties of Chinook Salmon Roe," Food Chemistry; 117(2):318-325; Nov. 15, 2009.
Buisson, D., et al., "Studies on Wax Esters in Fish," Chemical Processes in New Zealand, vol. II; Packer, J.E. (ed.); 1988; pp. 1-7; retrieved from http://nzic.org.nz/ChemProcesses/animal/5E.pdf on Apr. 25, 2013.
International Search Report of the ISA/US dated Dec. 7, 2012; Int'l Application No. PCT/US2012/053494 filed Aug. 31, 2012; Publication No. WO2013/033618A1 dated Mar. 7, 2013; 2pgs.

(Continued)

*Primary Examiner* — Marcela M Cordero Garcia
*Assistant Examiner* — Jia-Hai Lee
(74) *Attorney, Agent, or Firm* — Haukaas Fortius PLLC; Michael H. Haukaas

(57) ABSTRACT

The invention provides lipid compositions comprising phospholipids having a high docosahexaenoic acid (DHA) content, which compositions are preferably extracted from natural sources. The lipid compositions are excellent sources of highly bioavailable DHA and they can be used in oral delivery vehicles, dietary supplements, functional foods, and the like.

14 Claims, 2 Drawing Sheets

(56) References Cited

FOREIGN PATENT DOCUMENTS

| | | |
|---|---|---|
| WO | 2006111633 A2 | 10/2006 |
| WO | 2008060163 A1 | 5/2008 |
| WO | 2008117062 A1 | 10/2008 |
| WO | 2008149177 A2 | 12/2008 |
| WO | 2009156991 A2 | 12/2009 |
| WO | 2010039040 A1 | 4/2010 |
| WO | 2010136900 A2 | 12/2010 |
| WO | 2011011604 A2 | 1/2011 |
| WO | 2011050474 A1 | 5/2011 |
| WO | 2011112412 A1 | 9/2011 |
| WO | 2011137160 A2 | 11/2011 |
| WO | 2011151632 A1 | 12/2011 |
| WO | 2011119011 A9 | 3/2012 |

OTHER PUBLICATIONS

Sahena, F., et al., "PUFAs in Fish: Extraction, Fractionation, Importance in Health," Comprehensive Reviews in Food Science and Food Safety; 8(2):59-74; Mar. 23, 2009.

Written Opinion of the ISA/US dated Dec. 7, 2012; Int'l Application No. PCT/US2012/053494 filed Aug. 31, 2012; Publication No. WO2013/033618A1 dated Mar. 7, 2013; 5pgs.

\* cited by examiner

LIPID COMPOSITIONS WITH HIGH DHA CONTENT

RELATED APPLICATIONS

This application is a continuation of U.S. patent application Ser. No. 14/498,548, filed Sep. 26, 2014, issued as U.S. Pat. No. 9,458,409, which is a continuation of U.S. patent application Ser. No. 13/601,626, filed Aug. 31, 2012, issued as U.S. Pat. No. 8,846,604, which claims priority under 35 U.S.C. § 119(e) to U.S. Provisional Patent Application No. 61/530,648 filed Sep. 2, 2011 and 61/650,206 filed May 22, 2012, which applications are incorporated herein by reference.

BACKGROUND OF THE INVENTION

Omega-3 fatty acids are often referred to as "essential" fatty acids because they are needed for human health but are not sufficiently produced by the body alone. The two major health promoting omega-3 polyunsaturated fatty acids are eicosapentaenoic acid (EPA) and docosahexaenoic acid (DHA). EPA and DHA are naturally found in certain cold-water fatty fish such as salmon, tuna, and mackerel. They can also be derived in the body from alpha-linolenic acid (ALA), which is an omega-3 fatty acid found in certain seeds, plant-based oils, and animal-based oils. However, the body is very inefficient at converting ALA into EPA and DHA.

The modern diet is typically deficient in omega-3 essential fatty acids and has become overloaded with pro-inflammatory omega-6 fatty acids, especially arachidonic acid. This heavy imbalance of omega-6 to omega-3 fatty acids in the modern diet is thought to lead to an overall inflammatory state that contributes to several diseases. The increased consumption of vegetable oils and shortenings, beef, and dairy is one of the major reasons for the high amount of omega-6 fatty acids in the diet and the imbalance between omega-6 to omega-3 fatty acids. The North American population, in particular, has among the lowest dietary intake of omega-3 fatty acids in the world and the highest intake of the pro-inflammatory omega-6 fatty acids.

Adequate amounts of omega 3 fatty acids, including EPA and DHA, can be obtained in the diet from cold-water fatty fish such as salmon, tuna, and mackerel. However, larger fish species may contain high levels of mercury, polychlorinated biphenyls (PCBs), dioxins or other contaminants. Additionally, there is seasonal variability in the amounts of EPA and DHA found in these fish. Thus achieving an optimal and consistent amount of omega-3 fatty acids through the intake of fish alone raises a number of safety concerns. Fatty acids supplements are available. However, conventional over-the-counter omega-3 fatty acid supplements contain relatively impure material and are typically only about 30% omega-3 fatty acids. Furthermore, omega-3 fatty acids in supplements are often provided as free fatty acids, ethyl esters, or triglycerides, which may be inefficiently processed by the body. These non-polar ingredients can induce burping and discomfort, and require that larger amounts be consumed to gain any beneficial effect because of inefficiently processing.

Accordingly, there is a need for efficient processes for obtaining omega-3 phospholipids with high stability, good digestion properties, no safety and environmental concerns, without "fishy odor" and which are highly suitable for incorporation into dietary supplements, nutritional supplements and food products. There is also a need for new compositions that have a high ratio of omega-3 fatty acids compared to omega-6 fatty acids. There is further a need for compositions that include a high amount of DHA compared to EPA content.

SUMMARY

Docosahexaenoic acid (DHA) has important structural roles and also unique anti-inflammatory roles in the body. Most sources of omega-3 fatty acids are richer in EPA than DHA, therefore new sources of DHA rich fatty acids are needed. The invention described herein provides compositions having high DHA content, methods of obtaining such compositions, and methods of using such compositions, for example, for the treatment of various adverse conditions and diseases.

The invention thus relates to solid lipid compositions comprising a high content of EPA, n3-docosapentaenoic acid (n-3 DPA), and DHA. The compositions can be obtained from non-shellfish or non-crustacean sources. These lipid compositions are preferably extracted from natural sources such as immature fish roe. The compositions are useful as therapeutic compositions, food additives, and the like. They can also be combined with carrier oils and/or other additives to provide further useful products and therapeutic compositions.

Accordingly, the invention provides lipid compositions (e.g., a PL wax or PL oil) having high amounts of omega-3 phospholipids. A lipid composition can include about 50 wt. % to about 100 wt. % phospholipids. The omega-3 fatty acid content of the phospholipids can be at least about 25 wt. %, at least about 30 wt. %, at least about 40 wt. %, or at least about 45 wt. %, of the total fatty acids of the composition. For example, the lipid composition can include about 25 wt. % to about 50 wt. %, about 40 wt. % to about 50 wt. %, about 40 wt. % to about 55 wt. %, or about 35 wt. % to about 60 wt. %, of omega-3 fatty acids as a percentage of total fatty acids in the composition (e.g., about 27-32 wt. % free fatty acid equivalents in the wax).

The fatty acids of the lipid composition can include high amounts of DHA and EPA. The lipid composition can include DHA in an amount of about 20-40%, expressed as a percentage of total fatty acids in the composition and EPA in an amount of about 6-20%, expressed as a percentage of total fatty acids in the composition. In some embodiments, the lipid composition includes DHA in an amount of about 20-28%, expressed as a percentage of total fatty acids in the composition and EPA in amount of about 6-20%, expressed as a percentage of total fatty acids in the composition. In some embodiments, the DHA and EPA of the phospholipids can be present in a ratio of about 1.5:1 DHA:EPA to about 3.5:1 DHA:EPA. In other embodiments, the DHA:EPA ratio can be about 1.8:1 to about 2.5:1, or about 2.2:1 to about 2.8:1. The lipid composition can include less than about 1 wt. %, less than about 0.7 wt. %, or less than about 0.5 wt. %, of arachidonic acid.

The lipid composition can be a solid having a light brown or amber color. This solid phospholipid-rich composition can be referred to as a phospholipid wax, or PL wax. The lipid composition can also be a semisolid, or highly viscous oil (e.g., a PL oil), however the solid compositions can be more stable due to lower oxygen penetration.

The lipid composition can be obtained from a fish composition, such as fish internal organs, fish portions after processing, or fish roe. The fish roe can be mature fish roe or immature fish roe. The fish roe can be, for example, immature herring roe, immature salmon roe, immature mackerel roe, immature menhaden roe, or a combination thereof.

The lipid composition can be combined with other ingredients to formulate a dietary supplement, a nutritional supplement, a food product, or an oral delivery vehicle, for example, for a supplement or pharmaceutical product.

The lipid composition can be combined with a carrier oil, for example, an oil from a source other than the source of the polar lipid composition. The different source can be vegetable oil, krill oil, microbial oil, fish oil, or a combination thereof. The combination of the lipid composition and carrier oil can be referred to as a Marine Omega-3 Phospholipid composition, or MOPL. The MOPL can be an oil that is readily processed for a variety of uses.

The MOPL can include about 10 wt. % to about 90 wt. % of a PL wax or PL oil and about 10% to about 90% of a carrier oil. The carrier oil can include free fatty acids, mono-, di- and triglycerides, fatty acid ethyl esters, or a combination thereof.

In some embodiments, the invention provides a composition that includes a first phospholipid composition extract from fish roe and a second phospholipid composition extract from fish milt. A composition described herein can also include a fish protein additive.

The invention thus provides a solid phospholipid-rich lipid composition comprising greater than about 60% phospholipids, said phospholipids having about 25-40% or about 35-50% w/w DHA and EPA attached thereto, said DHA and EPA present in a ratio of about 1.5:1 DHA:EPA to about 3.0:1 DHA:EPA, wherein the lipid composition is a solid and is substantially stable to oxidation.

The invention also provides an emulsion that includes a PL wax as or PL oil as described herein, and water, and optionally a carrier oil. The emulsion can include, for example, about 0.1% to about 5% of the PL wax or MOPL.

In various embodiments, the invention provides a phospholipid composition (e.g., a PL wax or PL oil) as described above, wherein the phospholipids can comprise at least about 60 wt. %, at least about 65 wt. %, at least about 70 wt. %, or at least about 75 wt. %, of the composition. The composition can be rich in phosphatidylcholine content. For example, phosphatidylcholine can be at least about 45 wt. %, at least about 50 wt. %, at least about 54 wt. %, or about 55 wt. %, of the composition. Of the fatty acids in the composition, the fatty acids can have a greater percentage of DHA than EPA. For example, the ratio of DHA to EPA can be at least 1.1:1, at least 1.2:1, at least 1.3:1, or at least 2.5:1. Typically the ratio of DHA to EPA is at least about 1.5:1, up to about 3.5:1. The composition can also be low in arachidonic acid, for example, including less than about 10 mg/g, less than about 7 mg/g, less than about 5 mg/g, or less than about 4 mg/g. The composition can include about 10 ppm to about 1000 of Vitamin E, which can include various isomers of tocopherols and tocotrienols. The composition can also be free of shellfish antigens.

The invention further provides a process for efficiently providing a composition with high amounts of omega-3 phospholipids. The process can include contacting immature fish roe with a polar solvent; extracting a lipid fraction from the immature fish roe, to provide a mainly polar lipid fraction comprising omega-3 phospholipids; and removing the solvent from the lipid fraction comprising omega-3 phospholipids, to provide a solid, semisolid or highly viscous, mainly polar lipid composition comprising omega-3 phospholipids, wherein at least about 30%, at least about 40%, or at least about 50%, of the total fatty acids are omega-3 fatty acids (with respect to the phospholipids of the composition, or with respect to the total composition, or both). The solid polar lipid composition can be a PL wax as described above. A PL wax or PL oil can be combined with a carrier oil to provide a MOPL.

The invention yet further provides a process of extracting a phospholipid-enriched lipid composition from a fish or fish by-product. The process can include mixing fish, fish roe, or a fish-by product with a carrier lipid either before or after contacting the fish, fish roe, or fish by-product with a polar solvent, to form a lipid carrier composition; isolating a polar fraction from the carrier lipid composition; and removing solvent from the polar fraction to provide the phospholipid-enriched lipid composition.

The invention also provides a process of producing a solid phospholipid-rich lipid composition with a high content of DHA using the methods described herein, wherein the solid phospholipid lipid composition is substantially stable to oxidation. The invention also provides a method of providing oxidative stability in an emulsion comprising forming an emulsion with a PL wax or PL oil as described herein. The emulsion can be formed with water and, for example, about 0.1 wt. % to about 5 wt. % of the PL wax or PL oil.

The invention also provides methods of administering a polar lipid fraction or composition to a subject to provide a phospholipid composition to the subject, such as a phospholipid composition described herein. A variety of diseases and conditions can be treated or inhibited by administration of a phospholipid composition described herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DEFINITIONS

Definitions

Figure 1:
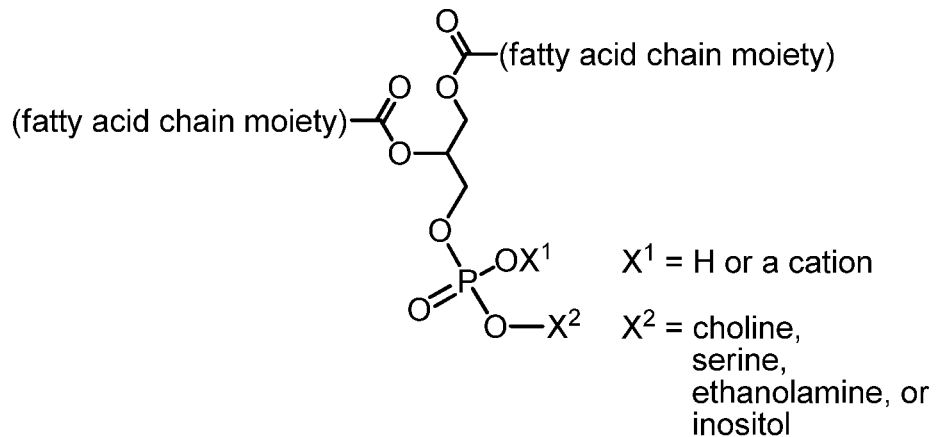
FIG. 1. An example of a phospholipid, according to one embodiment. One or the other fatty acid chain moiety and its associated carbonyl can be absent to provide hydroxyl groups in various embodiments. The fatty acid chain moieties can be, for example, EPA, DHA, or a group recited in Table 2-5.

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

A "fatty acid" refers to an alkanoic acid or an alkanoic acid moiety (i.e., the residue left after formal removal of the acid hydrogen), where the fatty acid includes at least about nine or ten carbon atoms. Non-limiting examples of fatty acids include decanoic acid (10:0), undecanoic acid (11:0), 10-undecanoic acid (11:1), lauric acid (12:0), cis-5-dodecanoic acid (12:1), tridecanoic acid (13:0), myristic acid (14:0), myristoleic acid (cis-9-tetradecenoic acid, 14:1), pentadecanoic acid (15:0), palmitic acid (16:0), palmitoleic acid (cis-9-hexadecenoic acid, 16:1), heptadecanoic acid (17:1), stearic acid (18:0), elaidic acid (trans-9-octadecenoic acid, 18:1), oleic acid (cis-9-octadecanoic acid, 18:1), nonadecanoic acid (19:0), eicosanoic acid (20:0), cis-11-eicosenoic acid (20:1), 11,14-eicosadienoic acid (20:2), heneicosanoic acid (21:0), docosanoic acid (22:0), erucic acid (cis-13-docosenoic acid, 22:1), tricosanoic acid (23:0), tetracosanoic acid (24:0), nervonic acid (24:1), pentacosanoic acid (25:0), hexacosanoic acid (26:0), heptacosanoic acid (27:0), octacosanoic acid (28:0), nonacosanoic acid (29:0), triacosanoic acid (30:0), trans vaccenic acid (trans-11-octadecenoic acid, 18:1), tariric acid (octadec-6-ynoic acid, 18:1), and ricinoleic acid (12-hydroxyoctadec-cis-9-enoic acid, 18:1) and $\omega_3$, $\omega_6$, and $\omega_9$ fatty acyl residues such as 9,12,15-octadecatrienoic acid (α-linolenic acid) [18:3, ω3]; 6,9,12,15-octadecatetraenoic acid (stearidonic acid) [18:4, ω3]; 11,14,17-eicosatrienoic acid (dihomo-.alpha.-linolenic acid) [20:3, ω3]; 8,11,14,17-eicosatetraenoic acid [20:4, ω3], 5,8,11,14,17-eicosapentaenoic acid [20:5, ω3]; 7,10,13,16,19-docosapentaenoic acid [22:5, ω3]; 4,7,10,13,16,19-docosahexaenoic acid [22:6, ω3]; 9,12-octadecadienoic acid (linoleic acid) [18:2, ω6]; 6,9,12-octadecatrienoic acid (γ-linolenic acid) [18:3, ω6]; 8,11,14-eicosatrienoic acid (dihomo-γ-linolenic acid) [20:3 ω6]; 5,8,11,14-eicosatetraenoic acid (arachidonic acid) [20:4, ω6]; 7,10,13,16-docosatetraenoic acid [22:4, ω6]; 4,7,10,13,16-docosapentaenoic acid [22:5, ω6]; 6,9-octadecadienoic acid [18:2, ω9]; 8,11-eicosadienoic acid [20:2, ω9]; 5,8,11-eicosatrienoic acid (Mead acid) [20:3, ω9]; trans-10,cis-12 octadecadienoic acid; cis-10,trans-12 octadecadienoic acid; cis-9,trans-11 octadecadienoic acid; and trans-9,cis-11 octadecadienoic acid. The acyl residues of a fatty acid moiety can also be conjugated, hydroxylated, epoxidized, and/or hydroxyepoxidized acyl residues.

An "omega-3 fatty acid" refers to a polyunsaturated fatty acid that has the final double bond in the hydrocarbon chain between the third and fourth carbon atoms from the methyl end of the molecule or moiety. Non-limiting examples of omega-3 fatty acids include Δ-5,8,11,14,17-eicosapentaenoic acid (EPA), Δ-4,7,10,13,16,19-docosahexanoic acid (DHA) and Δ-7,10,13,16,19-docosapentanoic acid (n-3 DPA).

The term "phospholipid" as used herein refers to a glycerol phosphate with an organic headgroup such as choline, serine, ethanolamine or inositol and either one or two fatty acids esterified to the glycerol backbone. See FIG. 1. Phospholipids include, but are not limited to, phosphatidylcholine, phosphatidylethanolamine, phosphatidylserine and phosphatidylinositol as well as corresponding lysophospholipids. For example, a "phospholipid" can refer to an organic compound of Formula I:

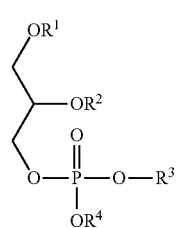

(I)

wherein $R^1$ is a fatty acid residue or H, $R^2$ is a fatty acid residue or H, $R^3$ is H or a nitrogen containing compound such as choline ($HOCH_2CH_2N^+(CH_3)_3OH^-$), ethanolamine ($HOCH_2CH_2NH_2$), inositol, or serine, and $R^4$ is a negative charge, H, or a cation such as an alkali metal cation (for example, $Li^+$, $Na^+$, or $K^+$). $R^1$ and $R^2$ are not simultaneously H. When $R^3$ is H, the compound is a diacylglycerophosphate (also known as phosphatidic acid), while when $R^3$ is a nitrogen-containing compound, the compound is a phosphatide such as lecithin, cephalin, phosphatidyl serine, or plasmalogen. The R1 site is referred to as position 1 of the phospholipid (per the stereospecific [sn] system of nomenclature), the R2 site is referred to as position 2 of the phospholipid (the sn2 position), and the R3 site is referred to as position 3 of the phospholipid (the sn3 position). Phospholipids also include phosphatidic acid and/or lysophosphatidic acid. Sphingolipids containing a phosphorus group are grossly classified as phospholipids; they contain a sphingosine base rather than a glycerol base.

The term "phospholipid wax" or "PL wax" refers to a mass of phospholipids that is a solid at room temperature (~23° C.). A PL wax as described herein can have a melting point interval in the range of about 28° C. to about 65° C. Some PL waxes can have a melting point interval in the range of about 28° C. to about 38° C., about 28° C. to about 35° C., about 28° C. to about 34° C., about 35° C. to about 65° C., about 40° C. to about 60° C., about 45° C. to about 55° C., or about 55° C. to about 65° C. Other PL waxes can have a melting point interval in the range of about 50° C. to about 60° C., about 40° C. to about 50° C., about 30° C. to about 40° C., about 30° C. to about 38° C., about 30° C. to about 35° C., or about 30° C. to about 33° C. The melting point interval can be an interval of about 2, about 3, about 4, about 5, about 7, or about 10° C. within one of the recited ranges. The PL wax can be pliable and the solid can be dissolvable in oils such as vegetable or fish oils.

As used herein, a "PL oil" refers to a viscous oil derived from a PL wax where the PL wax is further processed or purified to provide the viscous oil, rich in phospholipids.

As used herein, the term "lipid composition" refers to a wax or oil that can be extracted from a fish composition, especially immature fish roe. The lipid composition typically contains about 60-70 wt. %, about 62-67 wt. %, or about 63-66 wt. % of phospholipids, and certain neutral lipids and other components, for example, as outlined in Table 2-2. As would be readily recognized by one of skill in the art, the fatty acid profile of the phospholipids themselves will have a higher DHA and EPA content by weight than the overall lipid composition (e.g., a PL wax or PL oil) because of the presence of non-fatty acid components in such compositions.

The term "omega-3 phospholipid" as used herein refers to a to phospholipid molecule having an omega-3 fatty acid residue at the sn1 position, the sn2 position, or both positions, of a phospholipid molecule.

A composition having a "high amount" of omega-3 phospholipids refers to a composition where at least about 30 wt. % of the fatty acid groups on the phospholipid are omega-3 fatty acid moieties. A high amount of omega-3 phospholipid can also be a phospholipid composition where the fatty acid groups are the phospholipids are at least about 40 wt. % or at least about 50 wt. % omega-3 fatty acid groups, with respect to the total amount of fatty acids in the phospholipids of the composition.

The term "immature fish roe" as used herein refers to fish roe in which the eggs are primarily (e.g., greater than about 50%, greater than about 60%, greater than about 80%, or greater than about 90%) meiotic prophase arrest prior to maturation caused by a hormonal signal. Immature herring roe refers to roe collected between late October and the end of January, for example, in Norwegian waters; whereas mature roe is collected in February and March or later, for example, near the Norwegian coast. The Hjort maturity scale can be used to assess maturity of fish roe (see Hay et al., "Assessing and monitoring maturity and gonad development in Pacific herring"; *Can. Tech. Rep. of Fish and Aquat. Sci.*, Vol. 998; 1981; Government of Canada, Fisheries and Oceans). In all teleosts, oocytes appear to undergo the same basic pattern of growth, regardless of their reproductive strategy. The major developmental events occurring during oocyte development can be broadly classified into six phases, according to the state of oocytes growth; they are: oogenesis, primary oocyte growth, cortical alveolus stage, vitellogenesis, maturation and ovulation. During the early stages of oocyte development, DNA replication occurs (leptotene), homologous chromosomes pair (zygotene) and these pairs shorten and thicken (pachytene). The chromosomes then unpair into lampbrush configurations (diplotene), just before the oocyte enters a long period of cytoplasmic growth. The cytoplasmic growth of the oocyte is characterized by an enormous accumulation of yolk reserves (vitellogenesis). Meiosis resumes via a hormonal signal, and this leads to oocytes maturation. During this period, the nucleus, arrested in meiotic prophase, breaks down and the chromosomes enter first meiotic metaphase. The oocyte is then released from the ovary into the body cavity and it becomes an egg ready for fertilization. Generally, immature roe is roe prior to ovulation or swelling.

The terms "subject" and "patient" refer to any animal, particularly a mammal such as a dog, a cat, a bird, livestock, or a human.

The term "physiologically acceptable carrier" refers to any carrier or excipient commonly used with pharmaceuticals, and especially for oral delivery. Such carriers or excipients include, but are not limited to, oils, starch, sucrose and lactose as well as excipients for other delivery methods such as topical and parenteral delivery.

The term "oral delivery vehicle" refers to any means of delivering a desired composition orally, including, but not limited to, capsules, pills, tablets and syrups.

The term "emulsion" refers to a mixture of two or more liquids that are normally immiscible (non-mixable or unblendable, i.e., they do not form a solution). Emulsions are part of a more general class of two-phase systems of matter called colloids. The term emulsion is used when both the dispersed and the continuous phase are liquids, such as water and an oil, for example, a combination of a PL wax and a fish oil or other high DHA oil. In an emulsion, one liquid (the dispersed phase) is dispersed in the other (the continuous phase), to provide an oil-in-water (o/w) emulsion or a water-in-oil (w/o) emulsion. The phospholipid compositions described herein are typically provided as o/w emulsions. However, when using very high amounts of the phospholipid composition relative to water, a w/o emulsion can be prepared.

The term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

The term "foodstuff" refers to any substance fit for human or animal consumption. Examples include solid food, liquid food, combinations thereof, and beverages.

The term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

The term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

The term "functional food" refers to a food product to which a biologically active supplement, such as a phospholipid compositions described herein, has been added. A functional food is a food that has dietary or nutritional components at a higher amount of % RDA than naturally occurring food. A functional food can be a phospholipid-fortified medical food or conventional food.

The condition "dermatitis" refers to an inflammation of the skin such as a rash. Various forms of dermatitis may have common symptoms such as an allergic reaction to specific allergens. The term can include eczema, also referred to as dermatitis eczema and eczematous dermatitis. An eczema diagnosis can imply atopic dermatitis, common in children and teenagers. Dermatitis can refer to an acute condition whereas eczema refers to a chronic condition.

The condition "psoriasis" refers to an erythemo-scaly dermatitis of chronic evolution. Psoriasis is often characterized by thickened patches of reddish skin covered by slivery-white scales. The condition affects an estimated 2 percent of the population. With approximately 60,000 new cases diagnosed each year, it is one of the most prevalent skin diseases. It commonly appears as painful itching, cracked, and/or bleeding skin, which can affect over 10 percent of the body surface. It commonly manifests itself on the elbows, on the ulnar edge of the forearms, on knees, lower back, scalp, and nails. Severe psoriasis is known as erythrodermic psoriasis, psoriatic arthritis or pustular psoriasis. About 1.5 percent people develop psoriasis during childhood, before age 10, and 35 percent before age 20. This abnormality of the epidermis renewal is thus a serious affection, representing an important Public Health concern.

DETAILED DESCRIPTION

Omega-3 phospholipids are an important alternative to free fatty acid, methyl- and ethyl ester and triglyceride forms of omega-3 because they provide essential fatty acids in a more bioavailable form and they are processed by the body in a more efficient manner. However, current methods of obtaining phospholipids do not provide the high and consistent purity and high docosahexaenoic acid (DHA) content that is obtainable by the methods described herein. The invention thus provides efficient processes for obtaining omega-3 phospholipids with high stability, good digestion properties, no safety and environmental concerns, without "fishy odor" and which are highly suitable for incorporation into dietary supplements, nutritional supplements and food products.

It is well established in the art that the omega-6 fatty acid, arachidonic acid, competes for incorporation with omega-3 fatty acids for incorporation into phospholipid and other pools of lipids, diminishing the effectiveness of omega-3 fatty acids. For an omega-3 dietary preparation to be effective, the preparation must therefore contain very low levels of arachidonic acid, such as less than 1 wt. % of the total fatty acids in the product. Chicken egg-derived phospholipids and chicken egg-derived phosphatidylcholine provide phospholipids and the valuable nutrient choline, but do not provide appreciable levels of DHA and EPA, and unfortunately contain about 3 wt. % of arachidonic acid.

Another key advantage of phospholipid forms of omega-3 fatty acids over triglyceride forms of omega-3 fatty acids is that the former provides the key nutrient choline, which is lacking in many diets and contributes to proper liver function and reduction in homocysteine, a cholesterol-raising molecule. The importance of dietary choline is recognized by a claim permitted by the European Food Safety Authority (EFSA). Choline may be obtained in the diet, or converted from phosphatidylethanolamine in predominately liver cells via the enzyme phosphatidylethanolamine N-methyltransferase (PEMT). Both phosphatidylcholine and phosphatidylethanolamine, in specific ratios, are necessary to prevent fatty liver (steatosis or hepatosteatosis).

With increases in obesity, diabetes, and metabolic syndrome, steatosis is reaching epidemic proportions, and there are not effective drug treatments at this time. Steatosis can impair liver function, and progress to a further inflammatory condition of the liver known as non-alcoholic steatohepatitis (NASH). NASH in turn progresses to fibrosis then cirrhosis. Liver-related death is in fact a leading cause of mortality. Adequate supplies of dietary phosphatidylcholine and phosphatidylethanolamine can be of benefit in preventing and treating steatosis and the down stream sequelae described above.

Post-menopausal women and individuals with specific PEMT polymorphisms are unable to synthesize phosphatidylcholine adequately from phosphatidylethanolamine, and tend to have lower levels of hepatic phosphatidylcholine enriched with DHA. Thus, in these susceptible populations, it is particularly important that they receive adequate phosphatidylcholine enriched with DHA as present in wax PL and MOPL. As described above, both phosphatidylcholine and phosphatidylethanolamine are needed to prevent fatty liver. Moreover, phosphatidylethanolamine enriched with DHA is known to be a predominant source of hepatic phosphatidylcholine enriched with DHA, after PEMT conversion. Thus, it is desirable for the general population to receive DHA-enriched in both phosphatidylcholine and phosphatidylethanolamine, such as can be provided by the PL wax and MOPL.

Food allergies are a growing public health concern, with an estimated 9 million, or 4%, of adults in the United States having food allergies. The prevalence of food allergies and associated anaphylaxis appears to be on the rise. According to a study released in 2008 by the Centers for Disease Control and Prevention, an increase in food allergy of about 18% was seen in the United States between 1997 and 2007. Eight foods account for 90% of all food-allergic reactions. These include milk, eggs, peanuts, tree nuts, wheat, soy, fish, and shellfish. Allergic reactions to shellfish are generally a lifelong allergy. The estimated prevalence, some based on self-reporting, among the U.S. population is 0.4% for fish and 1.2% for crustacean shellfish. Shellfish allergies are likely underestimated because those sensitive to crustaceans may also be sensitive to mollusks and/or bivalves. In view of these data, the ideal phospholipid source of omega-3 fatty acids should be fish (roe, milt, body)-derived, rather than shellfish/crustacean/krill derived.

Figure 2:
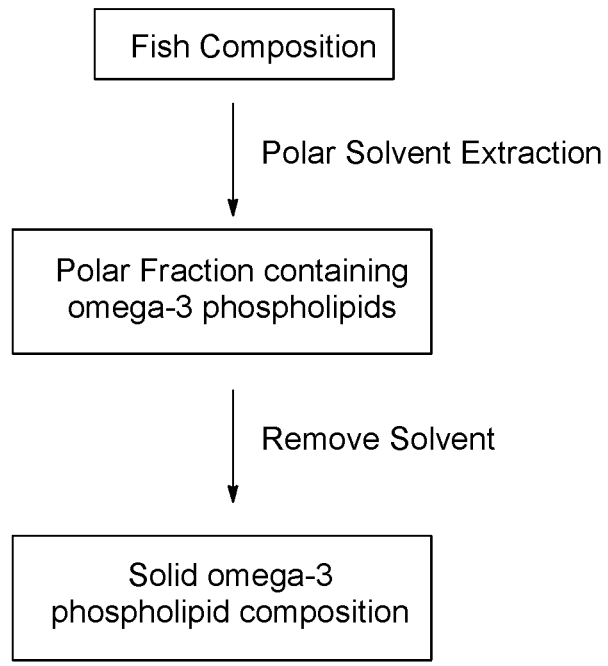
FIG. 2. An example of a process for obtaining a phospholipid composition from a fish composition, according to one embodiment.
Figure 3:
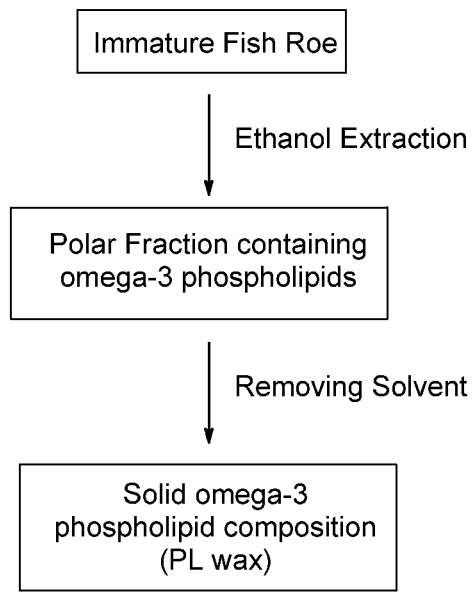
FIG. 3. An example of a specific process for obtaining a phospholipid composition from immature fish roe, according to one embodiment.
Figure 4:
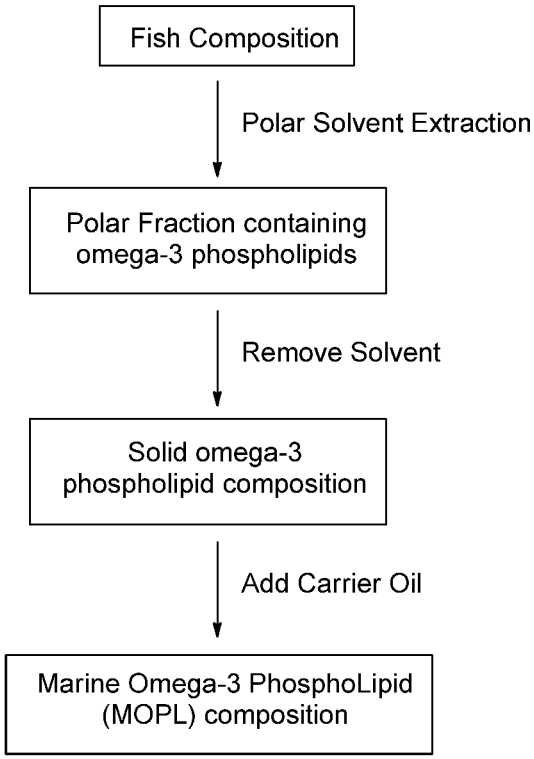
FIG. 4. An example of a process for preparing a phospholipid composition by combining a phospholipid composition obtained from a fish composition and a second lipid composition, according to one embodiment.

The invention thus relates to lipid compositions comprising a high content of DHA, which is preferably extracted from a natural source. Surprisingly, the inventors have found that stable, solid, phospholipid-rich lipid compositions with both a high phospholipid content and a high omega-3 fatty acid content, particularly enriched in DHA, can be efficiently prepared from fish and fish by-products, including immature fish roe, mature fish roe, milt and internal organs of fish. See for example, FIG. 2. The high omega-3 fatty acid content of the extracted phospholipids can include particularly high levels of EPA (eicosapentaenoic acid (20:5 (n-3))) and DHA (docosahexaenoic acid (22:6 (n-3))).

As discussed above, a PL wax can be extracted from a fish or fish by-product. In some embodiments, the fish is a cold water pelagic fish. In some embodiments, the fish by-product comprises fish roe. In some embodiments, the fish roe is immature fish roe. In some embodiments, the fish roe is mature fish roe. In some embodiments, the fish by-product is milt. In some embodiments, the fish by-product comprises fish internal organs. In some embodiments, the product is a mixture of roes, milts, and internal organs. The lipid composition can be substantially stable to oxidation. The stability of a composition to oxidation can be measured by accelerated shelf life tests, with oxidation determined using standard indices such as the amount of non-oxidized fatty acids remaining, and the presence of thiobarbituric acid reactive substances (TBARS), and peroxide value (PV) of the composition.

The solid polar lipid extracted from fish roe is known as "wax" or a "PL wax". Wax from mature and immature herring roe can contain phospholipids at about 60-70% by weight, with almost no variation related to maturity in the phospholipid content and the omega-3 fatty acid content. The PL wax can contain about 30-65% by weight of the long chain omega-3 fatty acids EPA, DHA, and n3 DPA, typically esterified to phospholipids, predominately phosphatidylcholine, with a typical ratio of DHA:EPA of 2-3:1. In various embodiments, the DHA and EPA can be present in a ratio of about 1.5:1 DHA:EPA to about 3:1 DHA:EPA, for example, about 1.7:1 DHA:EPA, about 1.8:1 DHA:EPA, or 2.5:1 DHA:EPA.

To produce a liquid oil product, the PL wax may be blended with a carrier oil. The carrier oil can be a vegetable oil, a fish oil, a krill oil, a microbial oil, or a combination thereof. The microbial oil can be an algal oil, a fungal oil, or the like, or a combination thereof. The carrier oil can also be a natural oil, or a chemically- or genetically-modified oil. The carrier oil can have a DHA:EPA ratio similar to the PL wax (i.e., +/−10% or 20%). In some embodiments, the process further comprises formulating a PL wax or a PL oil in an oral delivery vehicle, a topical delivery vehicle, a sub-lingual delivery vehicle, or a parenteral delivery vehicle.

In some embodiments, the oral delivery vehicle is a gel capsule. The oral delivery vehicle can be, for example, a chewable gel. In other embodiments, the invention provides a functional food product comprising a lipid composition described herein.

By blending the PL wax or PL oil with a carrier oil with a high DHA content, the ratio of DHA:EPA of 2-3:1 can be maintained, while providing a final product that is less viscous. Typical blends of a PL wax and fish oil (e.g., a MOPL) include 0.74-9 parts PL wax: 1 part fish oil. In one embodiment, the MOPL or "designer oil" can be prepared by combining about 10% to about 90% w/w of a PL wax and about 10% to about 90% of a second lipid fraction or "carrier oil". The carrier oil can include triglycerides, fatty acid ethyl esters, free fatty acids, or any combination thereof. Proper selection of the type, viscosity, and DHA:EPA content of the carrier oil enables one of skill in the art to provide a final product tailored to have certain physical and biochemical properties for specific purposes; other additives can be included in the designer oil such as conjugated linoleic acid, carnitine, and the like. For example, the carrier oil can be selected for certain desired properties such as fluidity, viscosity and overall fatty acid content (thereby forming a "designer oil" or "tailored oil"). Thus, the carrier oil can contain a high content of EPA or other desired fatty acid so that the level of EPA or other desired fatty acid in the composition can be increased as compared to DHA, or vice versa.

In some embodiments, a polar lipid fraction is extracted from a fish composition, such as immature fish roe, using a polar solvent such as ethanol. A carrier liquid can then be added to the polar lipid fraction and polar solvent to provide a carrier-enriched composition, for example, when the carrier is a fish oil or vegetable oil. Alternatively, water can be added to the polar lipid fraction and polar solvent to create an emulsion. Various amounts of ethanol may need to be removed before an effective emulsion can be prepared. The emulsion can include, for example, about 0.1% to about 5% of the PL wax, PL oil, or MOPL. In other embodiments, the emulsion includes about 0.2% to about 2.0% of the PL wax or PL oil. In yet other embodiments, an emulsion can be prepared with any amounts of PL wax and water, for example, varying from 1 part PL wax and 19 parts water, to 19 parts PL wax and 1 part water. Such emulsions thus provide a range of qualities and properties, and w/o emulsions as well as o/w emulsions. The PL wax can increase the oxidative stability of the emulsion, and in particular the oxidative stability of other lipids in the emulsion. Accordingly, in some embodiments, the invention provides methods for improving oxidative stability in an emulsion by forming an emulsion with a PL wax or PL oil as described herein.

The inventors have discovered that omega-3 phospholipids extracted from immature fish roe, a previously underutilized natural resource that is part of an existing fishery, have a desirable content of omega-3 fatty acids as described above, as well as having desirable physical properties that facilitate use for oral delivery and in nutritional supplements, dietary supplements, and food products. The omega-3 phospholipids can be, for example, extracted from immature fish roe, mature fish roe, milt, and internal organs. The invention is not limited to extraction of omega-3 phospholipids from any particular immature fish roe. However, in some embodiments, the immature fish roe is from herring, mackerel, menhaden, or salmon.

Extraction of omega-3 phospholipids may be accomplished by a variety of methods. For example, a polar solvent can be used for the extraction. In some embodiments, the polar solvent is ethanol. In other embodiments, the omega-3 phospholipids are extracted by super critical fluid extraction, preferably with a polar entrainer such as ethanol. Extraction with a polar solvent yields a polar lipid fraction that is enriched for omega-3 phospholipids. The solvent can be removed from the polar lipid fraction to provide a solid polar lipid composition that is enriched for omega-3 phospholipids. In various embodiments, extraction is by supercritical fluid extraction (SFE) using $CO_2$ as a solvent and ethanol as a polar entrainer. Some useful techniques for SFE are described by U.S. Patent Publication No. 2011/0160161 (Sampalis et al.).

The lipid compositions described herein are excellent source of DHA and EPA. The solid phospholipid-rich lipid compositions can also be pliable, and have a light brown or amber color. The solid phospholipid-rich lipid compositions are stable for extended periods of time, and for periods of time longer than corresponding fatty acids without phospholipid moieties, due to the antioxidant properties of the phospholipid moieties. The phospholipid compositions are highly suitable for formulation or incorporation into oral delivery vehicles, dietary supplements, nutritional supplements and food products. Accordingly the invention also provides processes for incorporating or formulating the lipid compositions described herein into desired products, such as those described below.

The invention also provides a PL wax, PL oil, or MOPL composition for administration to a subject, for example, to treat a condition or disease described herein. The polar lipid composition can also be used to improve the cognitive functioning of a subject. In other embodiments, the polar lipid fraction or composition is administered to a subject to treat or inhibit high blood triglycerides, high cholesterol, inflammation, hypertension, metabolic syndrome, obesity, other conditions recited herein, or a combination thereof.

Phospholipid Compositions

The invention provides various phospholipid compositions that have advantageous amounts and ratios of fatty acid esters. A phospholipid composition such as MOPL can include a combination of a triglyceride (e.g., a fish oil) and an extracted polar lipid rich in phospholipids (e.g., a PL wax). The combination can be present, for example, in a ratio ranging from about 1:10 to about 10:1. The phospholipids can have a structure such as Formula I:

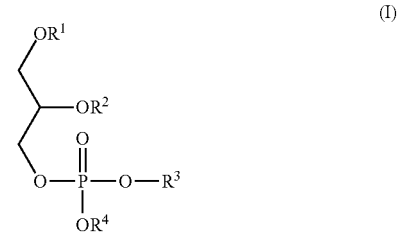

wherein $R^1$ is H or a fatty acid moiety, $R^2$ is H or a fatty acid moiety, each $R^3$ is independently H, or a choline, an ethanolamine, an inositol, a glycerol (as in phosphatidylglycerol or diphosphatidic acid), or a serine moiety, and $R^4$ is a negative charge, H, or a cation such as an alkali metal cation (for example, $Li^+$, $Na^+$, or $K^+$). In some embodiments, the phospholipid can have DHA and/or EPA moieties as at least 1% of the $R^1$, $R^2$, and $R^3$ groups. The phospholipids can have an overall concentration of OH groups on structures of Formula I in the range of about 2.5% to about 80%, about 5% to about 70%, about 10% to about 60%, or about 20% to about 50%.

In some embodiments, the omega-3 fatty acids moieties include EPA, DHA, n-3 DPA, and/or α-linolenic acid (ALA). In various embodiments, the composition is substantially free of organic solvents and volatile organic compounds such as short chain fatty acids, short chain aldehydes and short chain ketones (e.g., where short chain refers to $C_1$-$C_6$ alkyl).

In some embodiments, the phospholipid has at least 5%, or at least 10%, by weight, of a combination of EPA and DHA moieties esterified to the glycerol backbone. In various embodiments, the phospholipid has at least 20% of a combination of EPA and DHA moieties esterified to the glycerol backbone. The phospholipid can also have at least 30% of a combination of EPA and DHA moieties esterified to the glycerol backbone. In yet other embodiments, the phospholipid contains about 5%, about 10%, about 20%, about 30%, about 40%, or about 50% EPA/DHA moieties attached to position 1 and/or position 2 to the glycerol backbone. The remainder of the groups can be, for example, other fatty acids described herein or hydroxyl groups. In some embodiments, the phospholipid has a ratio of DHA:EPA ranging from about 1:1 to about 4:1. In other embodiments, the composition has a ratio of DHA:EPA ranging from about 2:1 to about 4:1. In other embodiments, fractionation and purification techniques can be used to produce a composition with a ratio of DHA:EPA of 10:1 or greater.

In some embodiments, glycerol oxygen atoms that are not phosphorylated in the composition can be about 30% to about 99% acylated, or about 40% to about 96% acylated. In other embodiments, the composition is acylated in a range from 50% to 78%. In yet other embodiments, the phospholipids are acylated to a degree of about 50% to about 90%, about 55% to about 85%, about 60% to about 80%, about 40% to about 80%, or about 55% to about 75%.

In some embodiments, the phospholipid extracted from fish roe can be a solid, such as a PL wax. In other embodiments, the phospholipid extracted from fish roe can be an oil, such as when the extraction process is modified to obtain only certain compounds or groups of compounds, for example, a PL oil.

The composition can be a marine lipid composition formulated into an animal feed, a food product, a food supplement, a drug delivery system, or a drug.

The composition that include the phospholipid can further include a lipid carrier. The lipid carrier can be present, for example, in a ratio of from 1:10 to 10:1 to PL wax or PL oil. In some embodiments, the lipid carrier and the PL wax or PL oil can be present in a ratio of about 5:1 to 1:5. In various embodiments, the composition includes about 20% to about 90% of the wax and about 10% to about 80% of the lipid carrier.

The various embodiments are not limited to any particular lipid carrier. In some embodiments, the lipid carrier is a triglyceride, a diglyceride, a monoglyceride, an ethyl ester, and a methyl ester, or a combination thereof.

In some embodiments, the invention provides methods of preparing a bioavailable omega-3 fatty acid composition. The methods can include a) providing a phospholipid composition that includes omega-3 fatty acid residues and optionally a triglyceride composition that includes omega-3 fatty acid residues; and b) combining the phospholipid composition and the triglyceride composition to form a bioavailable omega-3 fatty acid composition. The bioavailable phospholipid composition can be one of the compositions described above. In some embodiments, the methods further comprise encapsulating the bioavailable omega-3 fatty acid composition. In various embodiments, the bioavailable omega-3 fatty acid composition provides increased bioavailability compared to purified triglycerides or phospholipids comprising omega-3 fatty acid residues. The methods can further include packaging the bioavailable omega-3 fatty acid composition for use in compositions such as functional foods. The methods can also include assaying the bioavailable omega-3 fatty acid composition for bioavailability. In some embodiments, the methods further include administering the bioavailable omega-3 fatty acid composition to a patient. The invention also provides a food product, animal feed, food supplement or pharmaceutical composition made at least partially by one or more of the foregoing process.

In some embodiments, the composition can include a useful nutritional amount of cholesterol. Some compositions, such as a MOPL 50 product, can include about 3-10 g, about 4-8 g, about 4-6 g, about 6-8 g, about 5 g or 7 g, of cholesterol per 100 g sample. Other compositions, such as a MOPL 30 product, can include about 2-4 g, or about 3 g, of cholesterol per 100 g sample.

The compositions can also include an extremely low water content. A low water content can increase the stability and shelf life of the compositions, thereby providing a high purity product. In some embodiments, the phospholipid composition will include less than about 2 wt. % water, less than about 1 wt. % water, less than about 0.75 wt. % water, less than about 0.5 wt. % water, less than about 0.4 wt. % water, less than about 0.25 wt. % water, less than about 0.1 wt. % water, less than about 0.05 wt. % water, or less than about 0.01 wt. % water.

High levels of free fatty acids contribute to rancidity, off-taste, and increased oxidizability of food products and supplements. The phospholipid compositions described herein can be provided in a form containing very low or no free fatty acid content, due to the low naturally occurring levels in herring roe and the gentle and mild extraction and purification steps employed. The phospholipid compositions obtained from fish roe typically contain much lower amount of free fatty acids compared to products extracted from other sources such as krill, the extracts from which can include high amounts of free fatty acids (e.g., greater than about 3 wt. %, and as high as about 21-22 wt. %). The phospholipid compositions described herein can also include specific beneficial amounts of phospholipids and lysophospholipids not found in other extracts and compositions. For example, the phospholipid compositions described herein can include a lysophospholipid (e.g., a 1-acyl; 2-lyso; 1-lyso; 2-acyl; or di-lyso (phosphatidic acid); an alkylacyl PC and/or PE; an alkenylacyl PC and/or PE; and/or other phospholipids Such components are often ignored, such as phosphatidyl glycerol (PG) and diphosphatidylglycerol (DPG or cardiolipin), all of which are important bioactive lipids often ignored or not found in useful quantities in extractions from fish products or by-products. The extracts can also include astaxanthin (e.g., at about 1-1000 ppm).

The methods of efficiently extracting phospholipids from fish compositions such as fish roe provide a novel composition of solid phospholipids. While other phospholipids have been extracts from various fish compositions, the inventors have identified a unique set of phospholipids that can provide beneficial qualities to therapies and food products, where certain components are found in very high quantities, and other species are found in very low quantities or they are absent. Species-specific naturally low levels of free fatty acids combined with a gentle extraction technique have enabled the inventors to obtain a novel and advantageous phospholipid composition as described herein.

Thus, in some embodiments, with respect to the total mass of the PL wax, the PL wax can include at least about 50 wt. %, at least about 51 wt. %, or at least about 55 wt. % of phospholipids.

With respect to the total mass of phospholipids in the PL wax, the PL wax can include at least about 75 wt. %, at least about 80 wt. %, at least about 81 wt. %, or at least about 83 wt. % of phosphatidylcholine. With respect to the total mass of phospholipids in the PL wax, the PL wax can include less than about 5 wt. %, less than about 4 wt. %, less than about 3 wt. %, less than about 2.5 wt. % of phosphatidylinositol, or substantially no phosphatidylinositol (i.e., no detectable amount). With respect to the total mass of phospholipids in the PL wax, the PL wax can include about 5-10 wt. %, or about 6-9 wt. % of phosphatidylethanolamine. In other embodiments, the PL wax can include less than about 10 wt. %, less than about 9 wt. %, or less than about 8 wt. % of phosphatidylethanolamine. With respect to the total mass of phospholipids in the PL wax, the ratio of phosphatidylcholine to phosphatidylethanolamine can be from about 8:1 to about 17:1.

The PL wax can also have less than about 2 wt. %, less than about 1 wt. %, or no detectable phosphatidylserine, and less than about 2 wt. %, less than about 1 wt. %, or no detectable sphingomyelin.

The invention also provides a dietary supplement, a nutritional supplement or a food that includes a PL wax or MOPL composition described herein, or one made by a processes described herein. Thus, the invention provides an oral delivery vehicle, a topical delivery vehicle, a sublingual delivery vehicle, a parenteral delivery vehicle, or food made by a processes described herein, or that includes a compositions described herein.

To extract the phospholipids from the fish, fish by-products, or fish roe, any suitable and effective food grade polar solvent that is polar based on dielectric constant will suffice to effect a good extraction of the polar phospholipids. In some embodiments, the polar solvent is, for example, methanol, ethanol, butanol, or a combination thereof. In other embodiments, the extraction is a supercritical fluid extraction with a polar entrainer and/or a supercritical fluid solvent such as carbon dioxide.

The lipid compositions described herein can also include proteins or amino acids, such a protein from fish, from a fish by-product, or from fish roe, as described herein. The extracted solid lipid composition will typically have little (less than about 4 wt. %, less than about 3 wt. %, or less than about 0.5 wt. %) or no protein component because the proteins are poorly dissolved during the extraction process, and are typically filtered off. However, certain protein components or amino acids can be added to an emulsion prepared from the extracted phospholipid solid to provide a suitable and effective delivery vehicle for the protein or amino acids.

Methods of Extraction

A phospholipid composition can be extracted from fish composition, particularly fish roe. The fish component can be frozen and then ground and dried. The dried material can then be extracted with a suitable food-grade solvent, typically with stirring at ambient temperatures (~23° C.). It can be advantageous to break any egg shells to improve the efficiency of the extraction process. The solids of the mixture can then be separated, for example by decanting or the like. It can be advantageous to re-extract the solids at a higher concentration of the food-grade solvent, followed by separation of the solids from the extract. The extracts can then be optionally combined. The solvent can then be removed by any suitable and effective method. It can be advantageous to provide heat to enhance the evaporation, although the composition is typically heated to only 55° C. or less.

When the extract reaches approximately 10 wt. %, 15 wt. %, or 20 wt. % lipids, non-soluble solids can be removed by filtration. The lipid content of the extracts can be determined by evaporation of volatiles from a sample using a rotary evaporator under reduced pressure, or by infrared measurements. The solvent removal can be continued until the extract reaches about 50 wt. % to about 60 wt. % lipids, at which point the extract can be centrifuged to remove insoluble particles. The remaining solvent is then removed from the extract to provide a solid with a light amber color and a high content of phospholipids.

A phospholipid composition with an even higher content of phospholipids can be obtained by increasing the polarity of the extraction solvent. For example, instead of using 96% ethanol, a solvent with a higher percentage of water can be used, in order to extract a higher percentage of polar phospholipids, and thereby reducing the extraction of less polar components (e.g., certain fats and cholesterol).

Supplements and Food Products

The polar lipid compositions described herein can be used as a nutritional supplement, or it can be added to a food to provide a functional food. The phospholipid composition can be processed into a powder or granulated for such uses. Suitable methods include freeze drying the polar lipid composition in the presence of a suitable excipient. The resulting powder or granulated formulation can then be incorporated into oral delivery vehicles, dietary supplements, nutritional supplements, cosmetics, cosmeceuticals, and food products such as fortified foods and functional foods.

Suitable phospholipids can be obtained as described herein, such as from pelagic sources including herring roe. These extractions can be referred to as a PL was and they can be combined with a carrier oil to provide compositions referred to as Marine Omega-3 Phospholipids (MOPL). The phospholipid products can be kosher or halal when proper processing guidelines are followed, and they can be free of allergens such as shellfish allergens. The compositions can also advantageously be used in products such as infant formulas.

The invention also provides dietary supplements comprising the polar lipid compositions described above and processes for making the dietary supplements. Other nutraceuticals agents may also be included in the supplement. Nutraceutical agents are natural, bioactive chemical compounds that have health promoting, disease preventing or medicinal properties. Examples of nutraceuticals include, but are not limited to, *Allium cepa*, *Allium sativum*, *Aloe vera*, *Angelica* Species, Naturally Occurring Antioxidants, *Aspergillus oryzae*, barley grass, Bromelain, Carnitine, carotenoids and flavonoids, Catechin, *Centella asiatica* (Gotu kola), Coenzyme $Q_{10}$, Chinese Prepared Medicines, *Coleus forskohlii*, *Commiphora mukul*, Conjugated Linoleic Acids (CLAs), *Crataegus oxyacantha* (Hawthorne), *Curcuma longa* (Turmeric), *Echinacea* Species (Purple Coneflower), *Eleutherococcus senticosus* (Siberian Ginseng), *Ephedra* Species, Dietary Fish Oil, Genistein, *Ginkgo biloba*, *Glycyrrhiza* (Licorice), *Hypericum perforatum* (St. John's Wort), *Hydrastis* (Goldenseal) and other Berberine-containing plants, *Lactobacillus, Lobelia* (Indian Tobacco), *Melaleuca alternifolia*, Menaquinone, *Mentha piperita*, n-glycolylneuraminic acid (NGNA), *Panax Ginseng*, Pancreatic Enzymes, *Piper mythisticum*, Procyanidolic Oligomers, *Pygeum africanum*, Quercetin, Rosemary/Lemon balm, *Sarsaparilla* species, *Serenoa repens* (Saw palmetto, *Sabal serrulata*), *Silybum marianum* (Milk Thistle), Selenite, *Tabebuia avellanedae* (LaPacho), *Taraxacum officinale*, *Tanacetum parthenium* (Feverfew), Taxol, *Uva ursi* (Bearberry), *Vaccinium myrtillus* (Blueberry), *Valerian officinalis*, *Viscum album* (Mistletoe), Vitamin E, Vitamin A, Beta-Carotene and other carotenoids, and *Zingiber officinale* (Ginger).

Such compositions may contain, for example, a daily dosage of about 0.1 g to about 5.0 g of the polar lipid composition. Furthermore, the dietary supplement is preferably provided in an amount sufficient to induce the physiological response desired (e.g., treatment or prophylaxis of a condition such as high blood triglycerides, high cholesterol, inflammation, hypertension, metabolic syndrome, obesity, cognitive decline, memory loss, etc. A variety of uses is described in more detail below.

The dietary supplements of the invention are further useful in conjunction with a weight loss diet regimen. The invention is not limited to a particular kind of weight loss diet regimen (e.g., exercise, reduced calorie intake, etc.). In preferred embodiments, the weight loss diet regimen is a dietary plan (e.g., Atkins diet, Beverly Hills diet, Cabbage Soup diet, DietSmart.com diet, DietWatch.com diet, Fit For Life diet, Grapefruit diet, Herbalife diet, High Protein diet, Jenny Craig diet, Juice Fasts diet, Kashi GoLean diet, Low Fat diet, Mayo Clinic diet, Nutrisystem diet, Perricone diet, Pritkin diet, Ready to Eat diet, Revival Soy diet, Richard Simmons diet, Scarsdale diet, Shakes diet, Slim-Fast diet, Somersizing diet, South Beach diet, Special K diet, Subway diet, Sugar Busters diet, Thin For Life diet, Weight Watchers diet, and Zone diet). In still other preferred embodiments, the weight loss diet regimen is an exercise plan (e.g., running, swimming, meditation, yoga, clinical therapy, bicycling, walking, etc.). In still other preferred embodiments, the weight loss diet regimen is a clinically assisted plan (e.g., hypnosis, rehabilitory training, a dietary plan provided through a dietician, surgical procedures, etc.).

The dietary supplements of the invention may further be administered in any form (e.g., pill, food product, etc.). In preferred embodiments, the dietary supplements are provided as a beverage, bar, powder, pill, or shake (e.g., a nutritional supplement as described in more detail below).

The dietary supplements of the invention may be taken one or more times daily. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day (e.g., approximately 0.1-5 g of the polar lipid composition) in a reasonable number of units (e.g., two capsules or tablets taken twice a day). In preferred embodiments, the doses add up each day to the daily intake of each ingredient. In preferred embodiments, the dietary supplements are taken with meals or before meals. In other embodiments, the dietary supplements are not taken with meals.

Dietary supplements of the invention may be delivered in any suitable format, including, but not limited to, dermal delivery, oral delivery, or mucosal delivery. The ingredients of the dietary supplement can include pharmaceutically acceptable excipients and/or carriers for oral consumption, and in particular in the form of an oral delivery vehicle. The carrier may be a liquid, gel, gelcap, capsule, powder, solid tablet (coated or non-coated), tea, or the like. The dietary supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in Remington: The Science and Practice of Pharmacy, 21$^{st}$ Ed. (Lippincott Williams & Wilkins, Philadelphia, Pa.; 2005).

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The dietary supplement may comprise one or more inert ingredients, especially if it is desirable to limit the number of calories added to the diet by the dietary supplement. For example, the dietary supplement of the invention may also contain optional ingredients including, for example, herbs, vitamins, minerals, enhancers, colorants, sweeteners, flavorants, inert ingredients, and the like. For example, the dietary supplement of the invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), *spirulina*, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the invention provides nutritional supplements (e.g., energy bars or meal replacement bars or beverages) comprising the polar lipid compositions described above. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See *Modern Nutrition in Health and Disease*, eighth edition, Lea and Febiger, publishers, 1986, especially Volume 1, pages 30-32.

The nutritional supplement can also contain other ingredients, such as one or a combination of other vitamins, minerals, antioxidants, fiber and other dietary supplements (e.g., protein, amino acids, choline, lecithin, omega-3 fatty acids). Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

Servings of the nutritional supplement preferably contain for example, a daily dosage of between 0.1 g and 5.0 g of the polar lipid composition. It is understood by those of skill in the art that other ingredients can be added to those described herein, for example, fillers, emulsifiers, preservatives, etc. for the processing or manufacture of a nutritional supplement.

In still further embodiments, the invention provides functional foods, including food products, prepared food products, or foodstuffs comprising the polar lipid compositions described above. For example, in some embodiments, beverages and solid or semi-solid foods comprising the polar lipid compositions (or a powder or granulated formulation thereof) are provided. These forms can include, but are not limited to, beverages (e.g., soft drinks, milk and other dairy drinks, and diet drinks), baked goods, puddings, dairy products, confections, snack foods, or frozen confections or novelties (e.g., ice cream, milk shakes), prepared frozen meals, candy, snack products (e.g., chips), soups, spreads, sauces, salad dressings, prepared meat products, cheese, yogurt and any other fat or oil containing foods, and food ingredients (e.g., wheat flour). Servings of the food product preferably contain between 0.1 g and 5.0 g of the polar lipid composition.

Many important nutraceutical or cosmeceutical ingredients are poorly soluble in both aqueous compositions and lipophilic compositions. Such ingredients are also often poorly absorbed by the body. Examples include isoflavonoids and quercetin. Adding poorly soluble components to a MOPL composition or to an emulsion prepared from a PL wax or MOPL composition can improve their solubility, absorbability, and bio-efficacy. The nutraceutical or cosmeceutical ingredients can also be added to a phospholipid fraction extracted from fish composition, such as herring roe, prior to the removal of the polar solvent. The mixture can then be formulated into an emulsion or MOPL composition for providing improved solubility, absorbability, and bio-efficacy, as well as a high omega-3 content.

Pharmaceutical Formulations

The phospholipid compositions described herein can be used to prepare therapeutic pharmaceutical compositions. The phospholipid compositions are dispersible in water and oil, therefore they are amenable to a wide range of applications. Thus, the compositions described herein can be formulated as pharmaceutical compositions and administered to a mammalian host, such as a human patient, in a variety of forms. The forms can be specifically adapted to a chosen route of administration, e.g., topical, oral, or parenteral administration, such as by intravenous, intramuscular, or subcutaneous routes.

The compositions described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compositions may also be combined with one or more excipients and used in the form of ingestible tablets, buccal tablets, troches, capsules, elixirs, suspensions, syrups, wafers, and the like. Such formulations and preparations typically contain at least 0.1% of the phospholipid composition. The percentage of phospholipid in the compositions and preparations can vary and may conveniently be about 1% to about 99%, about 2% to about 90%, or about 2% to about 60% of the weight of a given unit dosage form. The amount of active in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the phospholipids may be incorporated into sustained-release preparations and devices.

In various embodiments, the phospholipids can be administered intravenously or intraperitoneally by infusion or injection. Dispersions of the phospholipids can be prepared in water, optionally mixed with a nontoxic surfactant. Solutions can be prepared in glycerol, liquid polyethylene glycols, triacetin, or mixtures thereof, or in a pharmaceutically acceptable oil. Under ordinary conditions of storage and use, preparations may contain one or more antioxidants or preservatives, for example, to prevent the growth of microorganisms.

Pharmaceutical dosage forms suitable for injection or infusion can include sterile aqueous solutions, dispersions, or sterile powders comprising the active phospholipids adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and/or suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the phospholipids in an appropriate amount in a suitable solvent, optionally with various other ingredients enumerated above, as required, followed by filter sterilization. In the case of sterile powders for the preparation of sterile injectable solutions, methods of preparation can include vacuum drying and freeze drying techniques, which yield a powder of the ingredient plus any additional desired ingredient present in the previously sterile-filtered solutions.

Topical Formulations.

For topical administration, phospholipids may be applied in pure form, e.g., as a PL wax or MOPL oil. However, it will generally be desirable to administer the phospholipids to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which the phospholipids can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Topical treatments, for example, in the form of ointments and creams, can be based on a composition described herein in combination with cortisone and/or vitamin D derivatives. Retinoids (vitamin A derivative) may also be used, alone or in combination with the with cortisone and/or vitamin D derivatives. These combinations are useful, for example, for treating psoriasis conditions such as small psoriasis lesions, or for treating a slow progression of psoriasis.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological ingredients and compositions can be used in combinations with the phospholipids described herein.

Formulation Dosage.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a composition required for use in treatment will vary not only with the particular set of phospholipids selected but also with the route of administration, the nature of the condition being treated, and the age and condition of the patient, and will be ultimately at the discretion of an attendant physician or clinician.

In some embodiments, the compound can be conveniently administered in a unit dosage form, for example, containing about 5 to 1000 mg/m$^2$, about 10 to 750 mg/m$^2$, or about 50 to 500 mg/m$^2$ of phospholipid ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Alternatively, an effective dosage amount of a phospholipid composition described herein can include, for example, about 300 mg to about 1000 mg of total omega-3 fatty acids. In various embodiments, the phospholipid composition can be administered orally. In other embodiments, the phospholipid composition can be administered topically. In some embodiments, the phospholipid composition is provided in a gel capsule or pill.

Therapy for Diseases and Adverse Conditions

Omega-3 fatty acids, in particular EPA and DHA, play a vital role in central nervous system, cognitive, cardiovascular, joint, immune, and metabolic functions. EPA and DHA not only protect good overall physical and emotional health, but also can reduce the risk of cardiac disease and exert powerful anti-inflammatory effects that can help treat certain diseases. The benefits of EPA and DHA have been studied across a wide range of illnesses, including, but not limited to, heart disease, high cholesterol, hypertension, arthritis, back pain, osteoporosis, psoriasis, lupus, Crohn's Disease, back pain, dry eyes, depression, bipolar disorder, ADHD, and stress-related disorders. Omega-3 fatty acids have also been shown to be important in pregnant women and infants, where their depletion can lead to visual or central nervous system problems. Additionally, omega-3 fatty acids are important for proper functioning in companion and husbandry animals. However, most sources of nutritional fats do not have a healthy ratio of omega-3 to omega-6 fatty acids. They also contain only low amounts of important omega-3 fatty acids such as DHA and EPA, and they are not highly bioavailable from those sources. The polar lipid compositions described herein can be used to provide concentrated amounts of omega-3 fatty acids that are highly bioavailable, which can aid the therapeutic treatment of many conditions, such as those described below.

Accordingly, the polar lipid compositions described herein have a wide variety of uses. The phospholipids have anti-inflammatory properties and have shown to be beneficial for brain health and cognitive performance. The phospholipid compositions are also beneficial for maintaining and improving gut health and cardiovascular health. For example, the polar lipid compositions are useful in modulating plasma triglyceride levels as well as plasma HDL C levels (the amount of cholesterol contained in HDL particles), while not elevating LDL C levels. Relevant diseases and disorders that can be treated include but are not limited to cardiometabolic disorders/metabolic syndrome (MetS), neurodevelopmental and neurodegenerative diseases/disorders, and inflammation disorders.

The invention thus provides methods of treating or preventing a cardiometabolic disorder/metabolic syndrome is provided, the method comprising administering to a subject in need thereof a polar lipid composition as described above. In some embodiments, the cardiometabolic disorder can be atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel, or diabetic autonomic neuropathy.

Methods of treating, preventing, or improving cognition and/or a cognitive disease, disorder or impairment (memory, concentration, learning (deficit)), or of treating or preventing neurodegenerative disorders are also provided. The methods can include administering to a subject in need thereof a polar lipid composition as described herein. In some embodiments, the cognitive disease, disorder or impairment is Attention Deficit Disorder (ADD), Attention Deficit Hyperactivity Disorder (ADHD), autism/autism spectrum disorder (ASD), dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson's disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well-being, neurodevelopmental, neurodegenerative disorders, hormonal disorders, neurological imbalance, or a combinations thereof. In a specific embodiment, the cognitive disorder is memory impairment. In some instances, the methods described above for treating, preventing, or improving cognition and/or a cognitive disease, disorder or impairment (memory, concentration, learning (deficit)), or of treating or preventing neurodegenerative disorders may utilize the polar lipid compositions described herein.

In some embodiments, methods for inhibiting, preventing, or treating inflammation or an inflammatory disease are provided, the methods comprising administering to a subject in need thereof, a polar lipid composition as described above. In some embodiments, the inflammation or inflammatory disease is selected from organ transplant rejection; reoxygenation injury resulting from organ transplantation (see Grupp et al., *J. Mol. Cell. Cardiol.* 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, Epilepsy, amyotrophic lateral sclerosis and viral or autoimmune encephalitis, preeclampsia; chronic liver failure, brain and spinal cord trauma, or cancer. The inflammatory disease can also be a systemic inflammation of the body, exemplified by gram-positive or gram negative shock, hemorrhagic or anaphylactic shock, or shock induced by cancer chemotherapy in response to proinflammatory cytokines, e.g., shock associated with proinflammatory cytokines. Such shock can be induced, e.g., by a chemotherapeutic agent that is administered as a treatment for cancer. Other disorders that can be treated include depression, obesity, allergic diseases, acute cardiovascular events, muscle wasting diseases, and cancer cachexia. Also, inflammation that results from surgery and trauma can be treated with the polar lipid compositions.

In some embodiments, the invention provides methods for reducing symptoms of cognitive dysfunction in a child. The methods can include administering an effective amount of a phospholipid composition described herein to a child in need of such symptom reduction. The symptoms can be, for example, one or more of the ability to complete task, ability to stay on task, ability to follow instructions, or ability to complete assignments. Administration of a composition described herein can improve psychomotor function, long term memory, short term memory, ability to make a decision, ability to follow through on decision, ability to self-sustain attention, ability to engage in conversations, sensitivity to surroundings, ability to plan, ability to carry out plan, ability to listen, interruptions in social situations, temper tantrums, level/frequency of frustration, level/frequency restlessness, frequency/level fidgeting, ability to exhibit delayed gratification, aggressiveness, demanding behavior/frequency of demanding behavior, sleep patterns, restive sleep, interrupted sleep, awakening behavior, disruptive behavior, ability to exhibit control in social situations, ability to extrapolate information and/or ability to integrate information. In some embodiments, the subject can exhibit one or more symptoms of Attention Deficit Hyperactivity Disorder (ADHD), can be suspected of having ADHD, or can have been diagnosed with ADHD. In some embodiments, the subject exhibits one or more symptoms of autistic spectrum disorder, is suspected of having autistic spectrum disorder, or has been diagnosed with autistic spectrum disorder.

In further embodiments, the invention provides methods of increasing cognitive performance in an aging mammal. The methods can include administering an effective amount of a phospholipid composition described herein. In some embodiments, the cognitive performance is memory loss, forgetfulness, short-term memory loss, aphasia, disorientation, disinhibition, or undesired behavioral changes.

The invention also provides methods of treating a subject by administration of a phospholipid composition described herein to a subject under conditions such that a desired condition is improved. The condition can be, for example, fertility, physical endurance, sports performance, muscle soreness, inflammation, auto-immune stimulation, metabolic syndrome, obesity, or type II diabetes.

In some embodiments, the invention provides methods for prophylactically treating a subject by administration of a phospholipid composition described herein to a subject under conditions such that an undesirable condition is prevented. The undesirable condition can be, for example, weight gain, infertility, obesity, metabolic syndrome, diabetes type II, mortality in subjects with a high risk of sudden cardiac death, or induction of sustained ventricular tachycardia. In some embodiments, the subject is at risk for developing a condition of weight gain, obesity, metabolic syndrome, diabetes type II, mortality in subjects with a high risk of sudden cardiac death, or induction of sustained ventricular tachycardia.

The compositions described herein can also be used for treating skin conditions such as common psoriasis, guttate psoriasis, nummular psoriasis, plaque psoriasis, erythrodermic psoriasis, psoriatic arthritis, pustular psoriasis, child psoriasis, parapsoriasis, acute or chronic dermatitis such as ichtiosis and keratose dermatitis, including palmoplantar keratoderma.

The subject or patient treated by the methods described herein can be a mammal. A mammal includes a primate, human, rodent, canine, feline, bovine, ovine, equine, swine, caprine, bovine and the like. In some embodiments, the mammal is a human. In some embodiments, the human is a male; in other embodiments, the human is a female. In certain embodiments, the subject is a companion animal. In yet other embodiments, the mammal is a pet such as a cat or dog. In further embodiments, the mammal has symptoms of age-associated memory impairment or decline.

The invention also provides phospholipid compositions that can be formulated into a feed product. Such feed products can reduce low-grade chronic inflammation in animals. The phospholipid compositions can also be formulated into a food product and given to humans for the same purpose. Furthermore, the phospholipid compositions can be formulated as a functional food product, as a drug or as food supplement.

Herring roe PL wax and MOPL are novel and convenient sources of EPA. They are also particularly good sources of DHA for infants. In addition, the phospholipid compositions described herein contain a highly available source of cholesterol for infants. Cholesterol is a key nutrient for infants and is lacking in vegetable oil-based infant formulas. Studies with sows demonstrated that the cholesterol in sow milk was much more bioavailable in the milk fat globule membrane (MFGM) than when added to infant formula. Therefore, the phospholipids in MOPL can make the cholesterol more bioavailable to those in need of cholesterol, such as infants. In addition, the phospholipid compositions also provide high bioavailability of other important dietary components such as choline.

The invention also provides therapeutic methods of treating cancer in a mammal. The methods can include administering to a mammal having cancer an effective amount of a composition described herein. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis. The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Example 1. Extraction of Phospholipids

Frozen, immature herring roe was ground and vacuum dried. The dried material was extracted with 96% ethanol at a ratio of 10 liters of ethanol per kg of dried roe in a stirred reactor at ambient temperature for 30 minutes. The stirring inside the reactor was combined with an external loop via a Silverson high shear mixer to break egg shells during the extraction. The solids and liquid extract were separated with a decanter. The solids were re-extracted with 96% ethanol, approximately 6 liters of ethanol per kg of dry weight eggs, for another 30 minutes. The solids and liquids were again separated in a decanter. The combined liquids (extracts) had a lipid content of around 5 wt. %, as determined by evaporation of volatiles from a sample using a rotary evaporator under reduced pressure. The lipid fraction was then concentrated by ethanol evaporation until reaching approximately 12% in a falling film evaporator at a temperature of less than 50° C. The lipid fraction was further concentrated by ethanol removal under reduced pressure in a stirred reactor. At a lipid content of around 20%, the ethanol solution was filtered to remove non-soluble solids. The concentration then continued until reaching approximately the 55% level at a temperature of less than 55° C. The 55% extract can then optionally be centrifuged to remove insoluble particles. The composition was then subjected to a final evaporation in a Gueudu mixer under reduced pressure. Pure ethanol can optionally be added and evaporated to assist the evaporation of final amounts of water to below 1%. The resulting product was a solid with a light amber color and a high content of phospholipids.

Example 2. Analysis of Phospholipid Composition Content

Extracted phospholipid compositions were in the form of a solid PL wax, which were analyzed for phospholipid mass balance and fatty acid content. The phospholipid compositions can be about 50% to about 95% phospholipids by weight. With further purification, the compositions can be about 90 wt. % to about 100 wt. % phospholipids. As can be observed from Table 2-1 below, phosphatidylcholine forms a large percentage of the phospholipid composition (e.g., a PL wax or a PL oil), for example, at least about 40 wt. %, at least about 50 wt. %, or at least about 54 wt. %. The composition also includes at least about 5 wt. %, or at least about 6 wt. % phosphatidylethanolamine. Table 2-1 uses standard abbreviations including APE for acyl phosphatidylethanolamine.

TABLE 2-1

Typical PL species as quantified by NMR.

| PL-class | No of FAs | MW | Typical weight % of PL wax |
|---|---|---|---|
| PC | 2 | 812 | 55.0 |
| 1-LPC | 1 | 534.5 | 0.4 |
| 2-LPC | 1 | 534.5 | 2.7 |
| PI | 2 | 907 | 0.8 |
| PE | 2 | 770 | 6.5 |
| LPE | 1 | 492.5 | 0.4 |
| APE | 3 | 1032 | 0.3 |
| other | 2 | 812 | 0.2 |
| Sum | | | 66 |

In some embodiments, the approximate mass balance of the composition can be as shown in Table 2-2 below.

TABLE 2-2

Approximate PL Wax Total Mass Balance.

| | |
|---|---|
| Fatty acids as mg TAG/g | 61 |
| Polar groups of PLs | 19 |
| Cholesterol | 7 |
| Ash content | 4 |
| Protein | 3 |
| Ethanol | 1 |
| Water | 0.5 |
| Other | 4.5 |
| Sum | 100 |

As shown in Table 2-3 below, the phospholipid compositions obtained by the methods described in Example 1 provide a composition with a high DHA:EPA ratio and low seasonal variability.

TABLE 2-3

Phospholipid Wax Phospholipid Composition Profile.

| Parameter | Conventional 18:12 Fish Oil | Krill Oil | PL Wax | Analysis |
|---|---|---|---|---|
| Content of ω-3 and phospholipids: | | | | |
| Total omega-3 as % of fatty acids | 30% | 30-35% | 42% | PL50 includes the highest omega-3 content available in current products |
| DHA:EPA ratio | 0.7 | ~0.6 | 2.7 | PL50 includes an extremely high DHA content |
| Seasonal variability in EPA and DHA | High | High | Low | Lowest seasonable variability of products analyzed |

TABLE 2-3-continued

Phospholipid Wax Phospholipid Composition Profile.

| Parameter | Conventional 18:12 Fish Oil | Krill Oil | PL Wax | Analysis |
|---|---|---|---|---|
| Contains MOPLs? | Trace | Yes | Yes | PL50 is a good source of MOPL and lecithin |
| Phospholipid content | Trace | 40-45% | >50% | PL50 has an extremely high content of phospholipids |

The phospholipid compositions have demonstrated excellent oxidative stability (with no addition of antioxidants) and they do not generate belching with fish aromas that is often associated with orally delivered conventional 18:12 fish oil (a common consumer complaint). The stability is not only superior to 18:12 fish oil but is also significantly superior to krill oil, which also has an inherently fishy odor that is much less noticeable in the phospholipid compositions described herein. Trace metals are not reported to concentrate in the roe, and there are no food chain or ecosystem concerns because the roe is a byproduct of existing fishery operations.

The phospholipid compositions can include a very low amount of free fatty acids (less than about 6.5 wt. %, less than about 5.5 wt. %, or less than about 1 wt. %), while krill oil can have as high as 21-22% of its EPA and DHA in free fatty acid form, which negatively affects bioavailability and/or leads to stability, oxidation, and sensorial problems.

Other phospholipid compositions, such as those described by U.S. Pat. No. 7,759,325 (Dupont), provide compositions that include lecithin at 10-50 wt. %, typically about 20 wt. %, of the composition. Of the total phospholipids, such compositions include 10-75% of phosphatidylcholine, 10-30% phosphatidyl inositol, 5-30% phosphatidylethanolamine, 5-20% phosphatidylserine, and 5-30% sphingomyelin, by weight. In various embodiments, the phospholipid compositions described herein do not include phosphatidylserine or sphingomyelin, or they are included in only very low amounts, and they include total phospholipid amounts of greater than 50% by weight.

A detailed analysis of fatty acids in a phospholipid extract (wax) provided the data shown in Table 2-4 below.

TABLE 2-4

Analysis of Fatty Acid Content.

| Fatty acid | Name | A % | mg/g wax |
|---|---|---|---|
| 14:0 | Myristic | 3.5 | 21.3 |
| 15:0 | pentadecanoic | 0.5 | 3.0 |
| 15:1 | pentadecenoic | 0.1 | 0.6 |
| 16:0 | Palmitic | 19.2 | 116.9 |
| 16:1 | palmitoleic | 5.6 | 34.1 |
| 16:2 | hexadecadienoic | 0.2 | 1.2 |
| 17:0 | heptadecanoic | 0.2 | 1.2 |
| 17:1 | heptadecenoic | 0.3 | 1.8 |
| 16:4 | hexadecatetraenoic | 0.1 | 0.6 |
| 18:0 | Stearic | 1.4 | 8.5 |
| 18:1 n-9 | Oleic | 8.4 | 51.2 |
| 18:1 n-7 | cis-vaccenic | 3.2 | 19.5 |
| 18:2 n-6 | Linoleic | 1.0 | 6.1 |
| 18:3 n-6 | γ-linolenic | 0.1 | 0.6 |
| 18:3 n-3 | α-linolenic | 0.7 | 4.3 |
| 18:4 n-3 | Stearidonic | 1.2 | 7.3 |
| 20:1 | eicosenoic | 1.8 | 11.0 |
| 20:2 n-6 | eicosadienoic (n6) (dihomolinoleic) | 0.1 | 0.6 |
| 20:4 n-6 | Arachidonic | 0.5 | 3.0 |
| 20:3 n-3 | eicosatrienoic (n3) (dihomolinolenic) | 0.1 | 0.6 |

TABLE 2-4-continued

Analysis of Fatty Acid Content.

| Fatty acid | Name | A % | mg/g wax |
|---|---|---|---|
| 20:4 n-3 | eicosatetraenoic (n3) | 0.6 | 3.7 |
| 20:5 n-3 | EPA | 12.8 | 77.5 |
| 22:1 n-11 | cetoleic | 0.5 | 3.0 |
| 22:1 n-9 | erucic | 0.1 | 0.6 |
| 21:5 n-3 | heneicosapentaenoic | 0.2 | 1.2 |
| 22:4 n-6 | docosatetraenoic (n6) (adrenic) | 0.2 | 1.2 |
| 22:5 n-6 | DPA n-6 | 0.2 | 1.2 |
| 22:5 n-3 | DPA n-3 | 1.0 | 6.1 |
| 22:6 n-3 | DHA | 31.3 | 191.8 |
| 24:1 | tetracosenoic | 0.6 | 3.7 |
| minor comp | minor sum | 4.3 | 26.2 |
| Sum fatty acids | | 100.0 | 609.7 |
| Total saturates | | 24.8 | 151.0 |
| Total monoenes | | 20.6 | 125.5 |
| Total n-3 | | 47.7 | 291.2 |
| Total n-6 | | 2.1 | 12.8 |
| n-3/n-6 | | 22.7 | |

Further analyses of various phospholipid waxes provided the data of Table 2-5.

TABLE 2-5

Approximate Fatty Acid Content in Phospholipid Waxes.

| Fatty acid(s) | In the phospholipids (approx. 65% of wax) Relative fatty acid composition (A %) | In the wax ("polar lipid composition") Relative fatty acid composition (A %) | Weight % |
|---|---|---|---|
| EPA | 6-20 | 6-20 | 4-12 |
| DHA | 20-40 | 20-40 | 12-24 |
| EPA + DHA | 26-60 | 35-50 | 16-36 |
| Total n-3 | 31-65 | 35-55 | 20-37 |
| DHA:EPA | 1.5-3.5 | 1.5-3.5 | 1.5-3.5 |

Thus, 1 g of wax will contain a total amount of fatty acids corresponding to around 610 mg of triglycerides. Another 190 mg of the remaining 390 mg can be accounted for by the polar moieties of the phospholipid molecules. Some variations from the actual content are a result of the analytical methods employed. Cholesterol also accounts for about 7 to about 8 wt. % of the total lipids in the wax obtained. Ethanol can comprise about 2 wt. % or less and water can be present in about 0.5 wt. % or less.

Example 3. Phospholipid Composition PL30 and PL50

The phospholipid compositions obtained as descried in Example 1 can be conveniently blended with a carrier such as a fish oil, for example, having a 17:54 EPA:DHA ratio, to provide a MOPL. A blend containing a minimum of 30 wt. % polar lipids is herein referred to as PL30, typically made by mixing wax and fish oil carrier approximately 50:50. A blend containing 50 wt. % polar lipids is herein referred to as PL50, typically made by mixing wax and fish oil carrier approximately 80:20. Ash content, primarily minerals, can comprise about 4-5 wt. % of the composition.

The PL30 and PL50 lipid compositions were further analyzed to determine their density, viscosity, flash points, and pour points. The data obtained is shown in the table below.

| Test | PL30 | PL50 |
|---|---|---|
| Density @ 20° C. (g/cm³) | 0.98 | 1.01 |
| Density @ 50° C. (g/cm³) | 0.96 | 0.98 |
| Kinematic Viscosity @ 20° C. (mm²/s) | 111.9 | * |
| Kinematic Viscosity @ 50° C. (mm²/s) | 33.29 | * |
| Flash Point, PMCC (° C.) | 130.0 | 55 |
| Pour Point (° C.) | −21 | −18 |

* Viscosity was greater than instrument analytical limits.

Example 4. Phospholipid Composition MOPL 50

A Marine Omega-3 Phospholipid (MOPL) composition was obtained from herring roe as described in Example 1 and was combined with fish oil triglycerides to optimize viscosity. Mixed tocopherols (300 ppm) were introduced with the fish oil as a natural food grade antioxidant. An 80:20 mixture of the extract (PL wax) and the fish oil triglycerides (carrier), respectively, will typically provide a MOPL 50 composition (>50% polar lipids).

An analysis of a set of phospholipids (a PL wax) obtained according to the methods of Example 1 also provided the data shown in Table 4-1 (where PC=phosphatidylcholine; 1-LPC=1-lysophosphatidylcholine; 2-LPC=2-lysophosphatidylcholine; PI=phosphatidylinositol; PE=phosphatidylethanolamine; LPE=lysophosphatidylethanolamine; and PS=phosphatidylserine), where the composition includes a fish oil carrier to provide PL50.

TABLE 4-1

PL Composition Analysis for a MOPL (PL50) Containing a Fish Oil Carrier.

| | | PL50 lots | |
|---|---|---|---|
| | Spec for PL50 | U041/ 008/A12 | ARC32414-1 | ARC32414-2 |
| Total PL amount PL groups (% w/w of product) | min 50 | 51.4 | 58.1 | 55.1 |
| PC | | 42.8 | 46.8 | 44.4 |
| 1-LPC | | 0.69 | 0.2 | 0.17 |
| 2-LPC | | 2.55 | 1.6 | 1.51 |
| Total PC | min 37.5 | 46.0 | 48.5 | 46.08 |
| PI | | nd | 1.3 | 1.24 |
| PE | | 4.5 | 3.9 | 3.54 |
| LPE | | 0.3 | nd | nd |
| Total PE | | 4.8 | 3.9 | 3.54 |
| PS | | nd | nd | nd |
| Sphingomyelin | | nd | nd | nd |
| PL groups (% w/w of total PL) | | | | |
| PC | | 83.2 | 80.5 | 80.6 |
| 1-LPC | | 1.3 | 0.3 | 0.3 |
| 2-LPC | | 5.0 | 2.7 | 2.7 |
| Total PC | | 89.5 | 83.5 | 83.6 |
| PI | | nd | 2.2 | 2.3 |
| PE | | 8.7 | 6.7 | 6.4 |
| LPE | | 0.6 | nd | nd |
| Total PE | | 9.4 | 6.7 | 6.4 |
| PS | | nd | nd | nd |
| Sphingomyelin | | nd | nd | nd | nd = not detected.

The product specification is in compliance with the EC regulations for food, and the GOED voluntary monograph regarding safety requirements (for environmental pollutants such as dioxins, PCB, and heavy metals). When stored in unopened closed containers under recommended storage conditions, the product has a shelf life of at least 36 months.

MOPL 50 Analytical Specifications:

| Parameter | Unit | Min. value | Max. value |
|---|---|---|---|
| Appearance | | Amber liquid oil | |
| Solubility | | Oil soluble and water dispersible | |
| EPA (C20:5 n-3) | Area % | 10 | |
| DHA (C22:6 n-3) | Area % | 27 | |
| Total omega-3[1)] | Area % | 42 | |
| EPA (C20:5 n-3) | mg/g | 70 | |
| DHA (C22:6 n-3) | mg/g | 190 | |
| Total omega-3[1)] | mg/g | 290 | |
| Total PC | mg/g | 375 | |
| Total PL | mg/g | 500 | |
| Total Neutral lipids | mg/g | | 500 |
| Water content by Karl Fisher | % | | 1.0 |
| Peroxide value | meq/kg | | 3.0 |
| Total plate count | cfu/g | | <100 |
| E. coli | /1 g | | negative |
| Salmonella | /25 g | | negative |
| Total Coliforms | cfu/g | | <10 |
| Yeast | cfu/g | | <10 |
| Molds | cfu/g | | <40 |
| Enterobacteria | negative/1 g | | negative |
| Staphylococci coagulase positive | negative/1 g | | negative |
| Dioxins and furans (PCDDs, PCDFs) | pg WHO-TEQ/g | | 2.0 |
| Dioxine-like PCBs | pg WHO-TEQ/g | | 3.0 |
| Dioxins + furans + Dioxine-like PCBs | pg WHO-TEQ/g | | 3.0 |
| Benzo(a)pyrene | ng/g | | 2.0 |
| Sum of benzo(a)pyrene, benz(a)anthracene, benzo(b)fluoranthene and chrysene | ng/g | | 10.0 |

| Parameter | Unit | Min. value | Max. value |
|---|---|---|---|
| PCBs IUPAC no. 28, 52, 101, 118, 138, 153, 180 | mg/kg | | 0.09 |
| Pb, Lead | mg/kg | | 0.1 |
| Hg, Mercury | mg/kg | | 0.01 |
| As, Arsenic | mg/kg | | 0.1 |
| Cd, Cadmium | mg/kg | | 0.1 |

[1])Total n-3: EPA, DHA, 18:3, 18:4, 20:4, 21:5, 22:5

Example 5. Pharmaceutical Dosage Forms

The following formulations illustrate representative pharmaceutical dosage forms that may be used for the therapeutic or prophylactic administration of a phospholipid composition described herein or a phospholipid composition specifically disclosed herein, such as a PL wax or a MOPL composition (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for treating psoriasis comprising orally administering to a subject diagnosed with psoriasis an effective amount of a lipid composition comprising phospholipids and a carrier oil, wherein:
the phospholipids comprise at least about 75 wt. % phosphatidylcholine; at least about 40% of the total fatty acids of the phospholipids are docosahexaenoic acid (DHA) and eicosapentaenoic acid (EPA); and the ratio of DHA to EPA is at least about 1.5:1;
the carrier oil comprises mono-, di- or triglycerides; fatty acid ethyl esters; free fatty acids; phospholipids, or a combination thereof; and
the lipid composition comprises about 20 wt. % to about 90 wt. % phospholipids and about 10 wt. % to about 80 wt. % carrier oil, and the composition is free of shellfish antigens;
wherein the administration is approximately daily for an effective amount of time to reduce the severity of the psoriasis, thereby treating or reducing the symptoms of the psoriasis.

2. The method of claim 1 wherein the psoriasis is common psoriasis, guttate psoriasis, nummular psoriasis, plaque psoriasis, erythrodermic psoriasis, psoriatic arthritis, pustular psoriasis, child psoriasis, or parapsoriasis.

3. The method of claim 1 wherein the phospholipids comprise omega-3 phospholipids and the omega-3 phospholipids comprise one or more of lysophosphatidylcholine, lysophosphatidylethanolamine, lysophosphatidylserine and lysophosphatidylinositol.

4. The method of claim 1 wherein the ratio of DHA to EPA in the phospholipids of the composition is at least about 2:1.

5. The method of claim 4 wherein the ratio of DHA to EPA in the phospholipids of the composition is about 2.2:1 to about 3.5:1.

6. The method of claim 1 wherein the lipid composition is administered in combination with the mineral zinc.

7. The method of claim 1 wherein the lipid composition is administered as part of a dietary supplement, nutritional supplement, pharmaceutical product, or food product.

8. The method of claim 7 wherein the supplement or product further comprises a fish protein additive.

9. The method of claim 8 wherein the fish protein additive comprises a fish protein hydrolysate or fish protein-derived amino acids.

10. The method of claim 1 wherein the lipid composition comprises about 50 wt. % carrier oil.

11. The method of claim 1 wherein the lipid composition comprises about 20 wt. % carrier oil.

12. The method of claim 1 wherein the carrier oil comprises fish oil, vegetable oil, krill oil, microbial oil, or a combination thereof.

13. The method of claim 1 wherein the composition comprises less than about 1 wt. % free fatty acids.

14. The method of claim 1 wherein the composition comprises less than about 0.5% arachidonic acid.

* * * * *